United States Patent
Van Nieuw Amerongen et al.

(10) Patent No.: US 6,638,531 B1
(45) Date of Patent: Oct. 28, 2003

(54) ANTIMICROBIAL PEPTIDES

(75) Inventors: Arie Van Nieuw Amerongen, Breukelen (NL); Engelmundus Cornelis Ignatius Veerman, Volendam (NL); Willem Van't Hof, Leiden (NL); Eva Josephine Helmerhorst, Amsterdam (NL)

(73) Assignee: Barnaux Healthcare B.V., Breda (NL)

(*) Notice: Subject to any disclaimer, the term of this patent is extended or adjusted under 35 U.S.C. 154(b) by 0 days.

(21) Appl. No.: 09/601,124

(22) PCT Filed: Jan. 26, 1999

(86) PCT No.: PCT/NL99/00045
§ 371 (c)(1),
(2), (4) Date: Oct. 13, 2000

(87) PCT Pub. No.: WO99/37678
PCT Pub. Date: Jul. 29, 1999

(30) Foreign Application Priority Data

Jan. 27, 1998 (NL) .............................. 1008139

(51) Int. Cl.[7] .......................... A61K 9/20; A61K 38/10; A61K 38/16; C07K 7/08; C07K 14/00
(52) U.S. Cl. .......................... 424/464; 514/12; 514/13; 514/14; 530/324; 530/325; 530/326; 530/327
(58) Field of Search .......................... 424/464; 514/12, 514/13, 14; 530/324, 325, 326, 327

(56) References Cited

FOREIGN PATENT DOCUMENTS

| WO | 9112815 | 9/1991 | .......... A61K/37/02 |
|---|---|---|---|
| WO | 9201462 | 2/1992 | .......... A61K/37/02 |
| WO | 9324138 | 12/1993 | .......... A61K/37/02 |
| WO | 9608270 | 3/1996 | .......... A61K/38/17 |
| WO | 9640251 | 12/1996 | .......... A61K/39/395 |

OTHER PUBLICATIONS

Takahashi et al.; "Synthesis of α–Helices Having a Positively Charged Random Coil–Block on Either N– or C–Terminal"; 1988; pp. 2467–2471; Bull Chemical Society, Japan, vol. 61.

Tossi et al.; "Identification and characterization of a primary antibacterial domain in CAP18, a lipopolysaccharide binding protein from rabbit leukocytes"; 1994; pp. 108–112; FEBS LETTERS, Federation of European Biochemical Societies, vol. 339.

Aoyagi et al.; "Synthesis of Antibacterial Peptides, Gramicidin S Analogs and Designed Amphiphilic Oligopeptides"; Jan. 1, 1998; pp. 877 to 886; Tetrahedron, vol. 44, No. 3.

Mihara et al.; "Design and Synthesis of Amphiphilic Basis Peptides with Antibacterial Activity and Their Interaction with Model Membrane"; 1987; pp. 697–706; Bull Chemical Society, Japan, vol. 60.

Helmerhorst et al.; "Synthetic histatin analogues with broad– spectrum antimicrobial activity"; 1997;, pp. 39–45 Biochem J., vol. 326.

Chemical Abstract: Mihara et al.; "Design and Synthesis of basic amphiphilic peptides possessing antimicrobial activity and their interaction with lipids", 106:214352 (1987).

Chemical Abstract: Sasaki et al.; Syntheses and properties of H–[Orn–Leu]n–OH (n=1–12) and cyclo [Orn–Leu–] n (n=2–8), 103:160837 (1985).

Van't Hof et al., *Epitope Mapping of the Dermatophagoides Pteronyssinus House Dust Mite Major Allergen Der p II Using Overlaping Synthetic Peptides, Molecular Immunology*, vol. 28, No. 11, pp. 1225–1232 (1991).

Primary Examiner—Jeffrey E. Russel
(74) Attorney, Agent, or Firm—Webb Ziesenheim Logsdon Orkin & Hanson, P.C.

(57) ABSTRACT

The present invention relates to peptides with antimicrobial activity, consisting of an amino acid chain which contains a domain of 10 to 25 amino acids, wherein the majority of the amino acids of the one half of the domain is positively charged amino acids and the majority of the amino acids of the other half of the domain is uncharged amino acids.

9 Claims, 5 Drawing Sheets

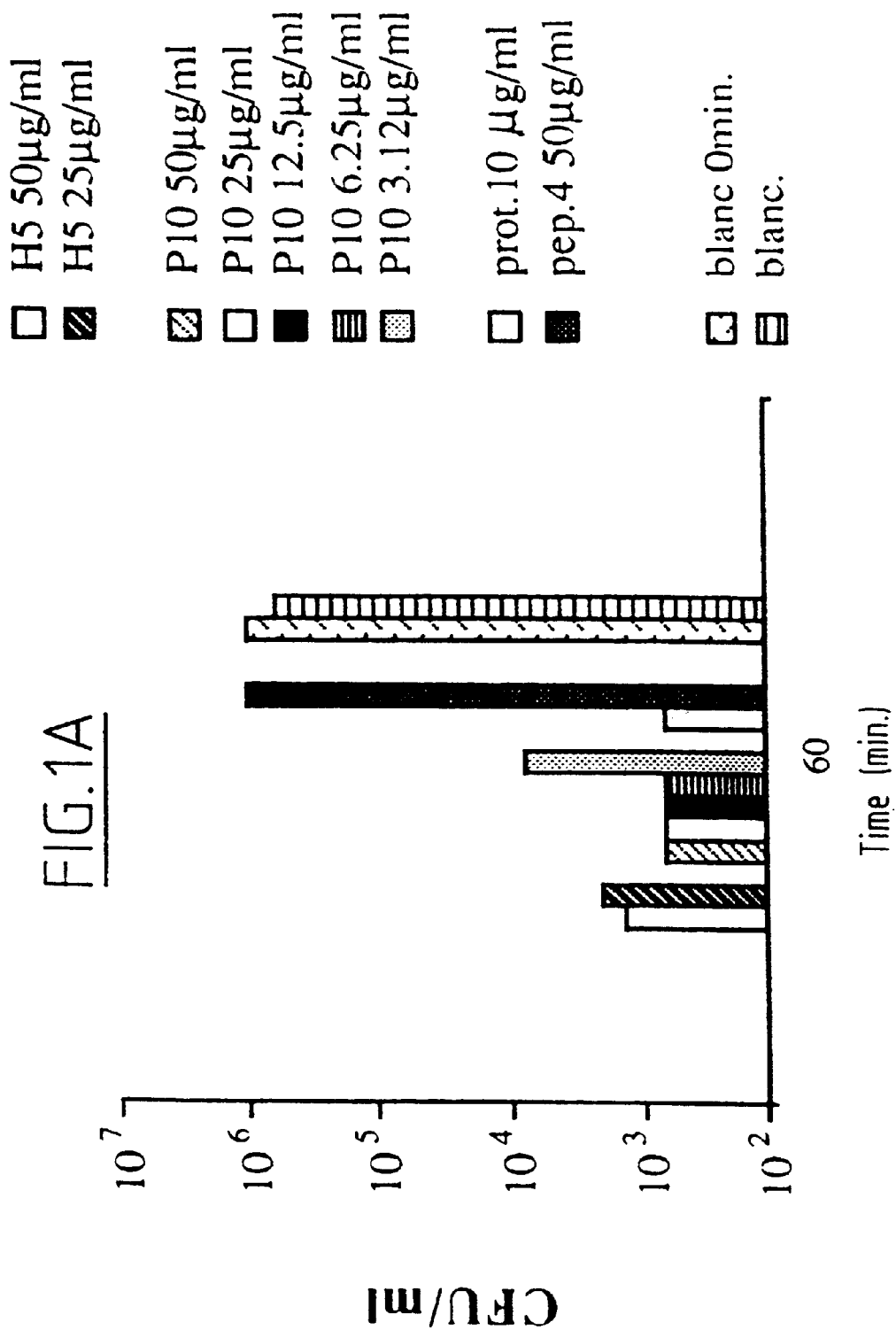

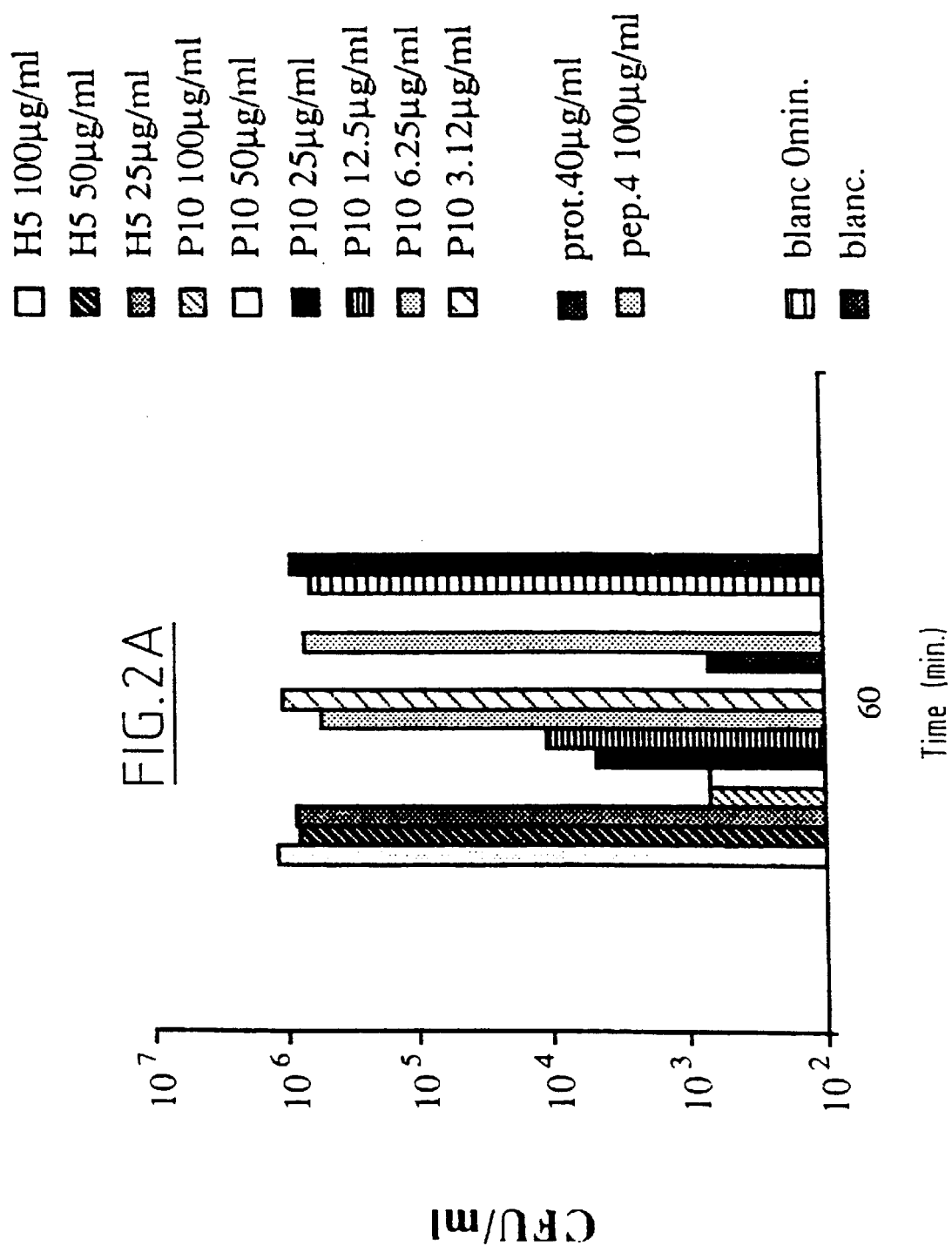

SEQUENCE LISTING

<160> NUMBER OF SEQ ID NOS: 21

<210> SEQ ID NO 1
<211> LENGTH: 14
<212> TYPE: PRT
<213> ORGANISM: Artificial Sequence
<220> FEATURE:
<223> OTHER INFORMATION: Peptide of Type I (hydrophobic on one side,
      hydrophilic on the other side) having antimicrobial activity

<400> SEQUENCE: 1

Lys Arg Leu Phe Lys Glu Leu Lys Phe Ser Leu Arg Lys Tyr
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Peptide of Type I (hydrophobic on one side,
      hydrophilic on the other side) having antimicrobial activity

<400> SEQUENCE: 2

Lys Arg Leu Phe Lys Glu Leu Leu Phe Ser Leu Arg Lys Tyr
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Peptide of Type I (hydrophobic on one side,
      hydrophilic on the other side) having antimicrobial activity

<400> SEQUENCE: 3

Lys Arg Leu Phe Lys Glu Leu Lys Lys Ser Leu Arg Lys Tyr
 1               5                  10

<210> SEQ ID NO 4
<211> LENGTH: 14
<212> TYPE: PRT
<213> ORGANISM: Artificial Sequence
<220> FEATURE:

```
<223> OTHER INFORMATION: Peptide of Type I (hydrophobic on one side,
      hydrophilic on the other side) having antimicrobial activity

<400> SEQUENCE: 4

Lys Arg Leu Phe Lys Glu Leu Leu Lys Ser Leu Arg Lys Tyr
 1               5                  10

<210> SEQ ID NO 5
<211> LENGTH: 14
<212> TYPE: PRT
<213> ORGANISM: Artificial Sequence
<220> FEATURE:
<221> NAME/KEY: SITE
<222> LOCATION: 1
<221> NAME/KEY: SITE
<222> LOCATION: 2
<221> NAME/KEY: SITE
<222> LOCATION: 5
<221> NAME/KEY: SITE
<222> LOCATION: 8
<221> NAME/KEY: SITE
<222> LOCATION: 9
<221> NAME/KEY: SITE
<222> LOCATION: 12
<221> NAME/KEY: SITE
<222> LOCATION: 13
<223> OTHER INFORMATION: Peptide of Type I (hydrophobic on one side,
      hydrophilic on the other side) having antimicrobial activity.
      Amino acids indicated by Xaa are ornithine.

<400> SEQUENCE: 5

Xaa Xaa Leu Phe Xaa Glu Leu Xaa Xaa Ser Leu Xaa Xaa Tyr
 1               5                  10

<210> SEQ ID NO 6
<211> LENGTH: 14
<212> TYPE: PRT
<213> ORGANISM: Artificial Sequence
<220> FEATURE:
<221> NAME/KEY: SITE
<222> LOCATION: 1
<221> NAME/KEY: SITE
<222> LOCATION: 2
<221> NAME/KEY: SITE
<222> LOCATION: 5
<221> NAME/KEY: SITE
<222> LOCATION: 9
<221> NAME/KEY: SITE
<222> LOCATION: 12
<221> NAME/KEY: SITE
<222> LOCATION: 13
<223> OTHER INFORMATION: Peptide of Type I (hydrophobic on one side,
      hydrophilic on the other side) having antimicrobial activity.
      Amino acids indicated by Xaa are ornithine.

<400> SEQUENCE: 6

Xaa Xaa Leu Phe Xaa Glu Leu Leu Xaa Ser Leu Xaa Xaa Tyr
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Peptide of Type I (hydrophobic on one side,
      hydrophilic on the other side) having antimicrobial activity

<400> SEQUENCE: 7

Lys Arg Leu Phe Lys Lys Leu Lys Phe Ser Leu Arg Lys Tyr
 1               5                  10
```

```
<210> SEQ ID NO 8
<211> LENGTH: 14
<212> TYPE: PRT
<213> ORGANISM: Artificial Sequence
<220> FEATURE:
<223> OTHER INFORMATION: Peptide of Type I (hydrophobic on one side,
      hydrophilic on the other side) having antimicrobial activity

<400> SEQUENCE: 8

Lys Arg Leu Phe Lys Lys Leu Leu Phe Ser Leu Arg Lys Tyr
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: Peptide of Type III (hydrophobic on the top,
      hydrophilic on the bottom) having antimicrobial activity

<400> SEQUENCE: 9

Leu Leu Leu Phe Leu Leu Lys Lys Arg Lys Lys Arg Lys Tyr
 1               5                  10

<210> SEQ ID NO 10
<211> LENGTH: 14
<212> TYPE: PRT
<213> ORGANISM: Artificial Sequence
<220> FEATURE:
<221> NAME/KEY: BINDING
<222> LOCATION: 14
<223> OTHER INFORMATION: Modified peptide having antimicrobial activity.
      Modifications are for instance an N-terminal amide ring, for
      instance with acetic anhydride, or an alternative cleavage of the
      synthesis resin by which the C-terminus is modified.

<400> SEQUENCE: 10

Lys Arg Leu Phe Lys Glu Leu Phe Phe Ser Leu Arg Lys Tyr
 1               5                  10

<210> SEQ ID NO 11
<211> LENGTH: 14
<212> TYPE: PRT
<213> ORGANISM: Artificial Sequence
<220> FEATURE:
<221> NAME/KEY: BINDING
<222> LOCATION: 14
<223> OTHER INFORMATION: Modified peptide having antimicrobial activity.
      Modifications are for instance an N-terminal amide ring, for
      instance with acetic anhydride, or an alternative cleavage of the
      synthesis resin by which the C-terminus is modified.

<400> SEQUENCE: 11

Lys Arg Leu Phe Lys Glu Leu Leu Phe Ser Leu Arg Lys Tyr
 1               5                  10

<210> SEQ ID NO 12
<211> LENGTH: 15
<212> TYPE: PRT
<213> ORGANISM: Artificial Sequence
<220> FEATURE:
<221> NAME/KEY: BINDING
<222> LOCATION: 15
<223> OTHER INFORMATION: Modified peptide having antimicrobial activity.
      Head-to-head or tail-to-tail coupling to form an oligomer occurs
      at this point.

<400> SEQUENCE: 12

Lys Arg Lys Phe His Glu Lys His His Ser His Arg Gly Tyr Cys
 1               5                  10                  15
```

```
<210> SEQ ID NO 13
<211> LENGTH: 15
<212> TYPE: PRT
<213> ORGANISM: Artificial Sequence
<220> FEATURE:
<221> NAME/KEY: BINDING
<222> LOCATION: 15
<223> OTHER INFORMATION: Modified peptide having antimicrobial activity.
      Head-to-head or tail-to-tail coupling to form an oligomer occurs
      at this point.

<400> SEQUENCE: 13

Tyr Gly Arg His Ser His His Lys Glu His Phe Lys Arg Lys Cys
  1               5                  10                  15

<210> SEQ ID NO 14
<211> LENGTH: 14
<212> TYPE: PRT
<213> ORGANISM: Artificial Sequence
<220> FEATURE:
<221> NAME/KEY: BINDING
<222> LOCATION: 14
<223> OTHER INFORMATION: Modified peptide having antimicrobial activity.
      Two identical amino acid chains of this composition are linked to
      one substituted lysine molecule at this point.

<400> SEQUENCE: 14

Lys Arg Lys Phe His Glu Lys His His Ser His Arg Gly Tyr
  1               5                  10

<210> SEQ ID NO 15
<211> LENGTH: 14
<212> TYPE: PRT
<213> ORGANISM: Artificial Sequence
<220> FEATURE:
<221> NAME/KEY: BINDING
<222> LOCATION: 14
<223> OTHER INFORMATION: Modified peptide having antimicrobial activity
      Two identical amino acid chains of this composition are linked to
      one substituted lysine molecule at this point.

<400> SEQUENCE: 15

Lys Arg Leu Phe Lys Glu Leu Lys Phe Ser Leu Arg Lys Tyr
  1               5                  10

<210> SEQ ID NO 16
<211> LENGTH: 14
<212> TYPE: PRT
<213> ORGANISM: Artificial Sequence
<220> FEATURE:
<221> NAME/KEY: BINDING
<222> LOCATION: 14
<223> OTHER INFORMATION: Modified peptide having antimicrobial activity
      Two identical amino acid chains of this composition are linked to
      one substituted lysine molecule at this point.

<400> SEQUENCE: 16

Lys Arg Leu Phe Lys Lys Leu Lys Phe Ser Leu Arg Lys Tyr
  1               5                  10
```

```
<210> SEQ ID NO 17
<211> LENGTH: 24
<212> TYPE: PRT
<213> ORGANISM: Homo sapiens
<220> FEATURE:
<223> OTHER INFORMATION: Histatin-5, a salivary peptide

<400> SEQUENCE: 17

Asp Ser His Ala Lys Arg His His Gly Tyr Lys Arg Lys Phe His Glu
 1               5                  10                  15

Lys His His Ser His Arg Gly Tyr
            20

<210> SEQ ID NO 18
<211> LENGTH: 14
<212> TYPE: PRT
<213> ORGANISM: Homo sapiens
<220> FEATURE:
<223> OTHER INFORMATION: C-terminal portion of Histatin-5, a salivary
      peptide

<400> SEQUENCE: 18

Lys Arg Lys Phe His Glu Lys His His Ser His Arg Gly Tyr
 1               5                  10

<210> SEQ ID NO 19
<211> LENGTH: 20
<212> TYPE: PRT
<213> ORGANISM: Artificial Sequence
<220> FEATURE:
<221> NAME/KEY: BINDING
<222> LOCATION: 20
<223> OTHER INFORMATION: Synthetic Protein beginning with Glycine and
      ending with Leucin-amide.  Amide substituent at site indicated.

<400> SEQUENCE: 19

Gly Met Ala Ser Lys Gly Ala Ile Ala Gly Lys Ile Ala Lys Val Ala
 1               5                  10                  15

Leu Lys Ala Leu
            20

<210> SEQ ID NO 20
<211> LENGTH: 14
<212> TYPE: PRT
<213> ORGANISM: Artificial Sequence
<220> FEATURE:
<223> OTHER INFORMATION: Peptide consisting of the residues 1 to 14 of
      synthetic cystatin S.

<400> SEQUENCE: 20

Ser Ser Ser Lys Glu Glu Asn Arg Ile Ile Pro Gly Gly Ile
 1               5                  10

<210> SEQ ID NO 21
<211> LENGTH: 19
<212> TYPE: PRT
<213> ORGANISM: Homo Sapiens
<220> FEATURE:
<223> OTHER INFORMATION: Inactive peptide of the Von Ebner's Gland
      Protein (VEGh)

<400> SEQUENCE: 21

Leu Leu Ala Ser Asp Glu Glu Ile Gln Asp Val Ser Gly Thr Trp Tyr
 1               5                  10                  15

Leu Lys Ala
```

ANTIMICROBIAL PEPTIDES

Figure 1B:
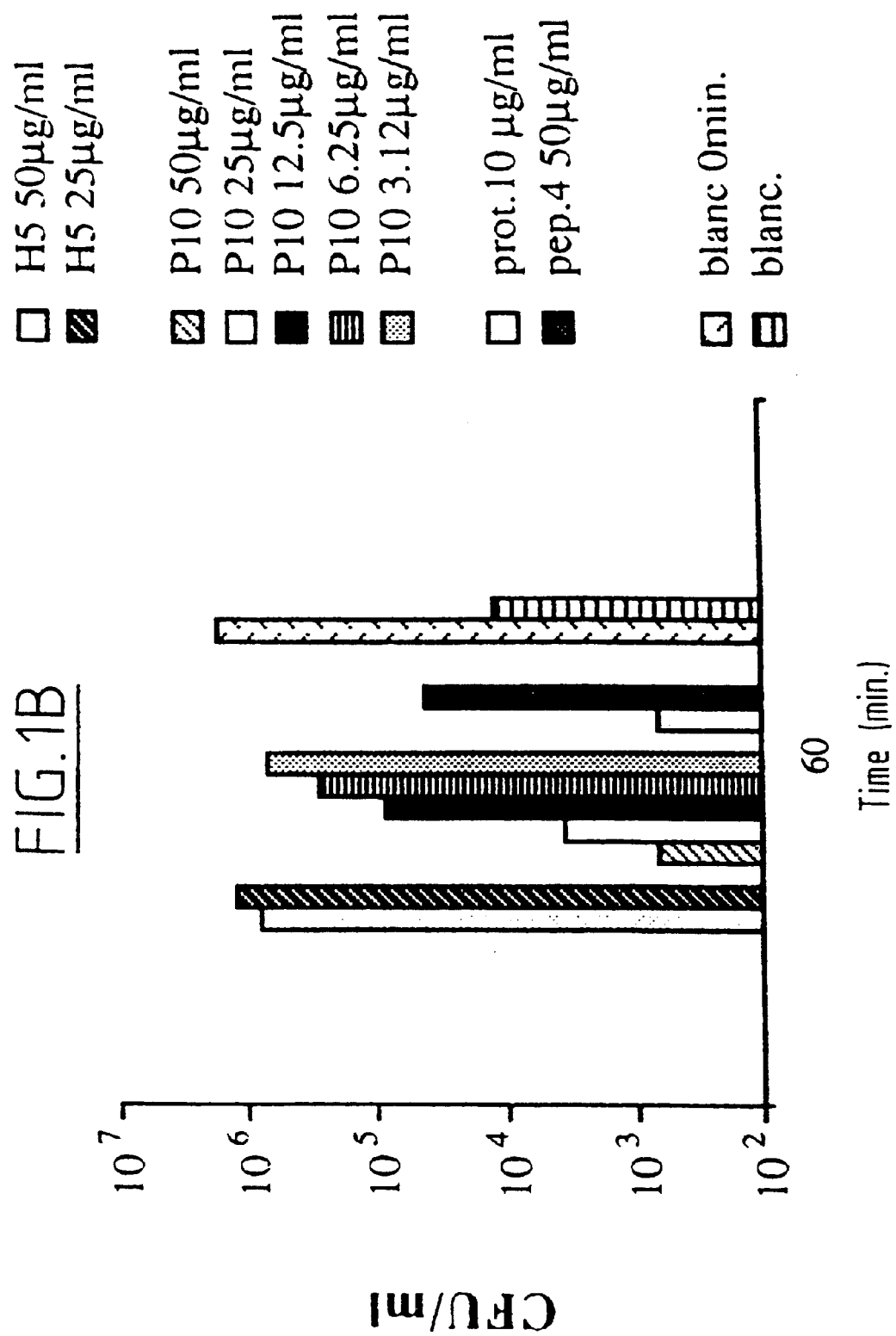

The present invention relates to new peptides with an antimicrobial activity. The antimicrobial activity is particularly aimed at bacteria, fungi and yeasts.

The use of the known antibiotics is in an increasing number of cases no longer sufficient for the treatment of infections. Many bacteria strains have developed resistance to the known classes of antibiotic and in the last thirty years no new classes of antibiotic have been discovered. In view of the above, a new class of antimicrobial agents is very desirable. Alkaline peptides and proteins are found in saliva which have a bactericidal and fungicidal activity in vitro. Histatins form a known family of such salivary peptides. However, in order to be clinically applicable as well it is desirable that the antimicrobial activity is even higher. A higher activity compensates the proteolytic degradation of the agent which always occurs to a greater or lesser degree. Furthermore, a reduced proteolytic degradation relative to the naturally occurring peptides is desirable. Finally, from an economic point of view in respect of the production of the peptides, it is recommended that antimicrobial agents are relatively small.

It is the object of the present invention to provide new antibacterial and antifungal agents which do not have the above stated drawbacks and which comply as far as possible with the recommended requirements.

This is achieved with the invention by peptides consisting of an amino acid chain which contains a domain of 10 to 25 amino acids, wherein the majority of the amino acids of the one half of the domain are positively charged amino acids and the majority of the other half of the domain are uncharged amino acids.

The structure of these peptides has a number of variations. Firstly, the domain can form an α-helix, of which at least a majority of the positions 1, 2, 5, 6, 9 (12, 13, 16, 19, 20, 23 and 24) contains a positively charged amino acid, position 8 is a positive or an uncharged amino acid and at least a majority of the positions 3, 4, 7, 10, (11, 14, 15, 17, 18, 21, 22, 25) contains an uncharged amino acid. These peptides have a lateral amphipathicity, i.e. a maximum hydrophobic moment at 100°. Stated simply, these peptides are hydrophobic on the left side and hydrophilic on the right side or vice versa. These peptides are referred to herein as "type I".

The domain can further form an α-helix, of which at least a majority of the positions 1, 2, 5, 6, 9 (12, 13, 16, 19, 20, 23 and 24) contains an uncharged amino acid, position 8 is a positive or an uncharged amino acid and at least a majority of the positions 3, 4, 7, 10, (11, 14, 15, 17, 18, 21, 22, 25) contains a positively charged amino acid. These peptides have a lateral amphipathicity, i.e. a maximum hydrophobic moment at 100°. Stated simply, these peptides are hydrophobic on the right side and hydrophilic on the left side or vice versa. These peptides are designated "type II" herein and are in principle mirror-symmetrical to type I peptides.

In addition, the domain can form an α-helix, wherein at least a majority of the positions 1 to 6 (or 7 or 8 or 9 or 10 or 11 or 12) contains an uncharged amino acid and a positively charged amino acid is found at position 7 (or 8 or 9 or 10 or 11 or 12 or 13) to 25. These peptides have a longitudinal amphipathicity, i.e. a minimum hydrophobic moment at 100°. These peptides are hydrophobic on their "top" and hydrophilic on their "bottom". Such peptides are designated "type III".

Conversely, the domain can form an α-helix, wherein at least a majority of the positions 1 to 6 (or 7 or 8 or 9 or 10 or 11 or 12) contains a positively charged amino acid and an uncharged amino acid is found at position 7 (or 8 or 9 or 10 or 11 or 12 or 13) to 25. These peptides likewise have a longitudinal amphipathicity and therefore a minimum hydrophobic moment at 100°. These peptides are hydrophobic on their "bottom" and hydrophilic on their "top". Such peptides are designated "type IV".

Finally, the domain can form a so-called β-strand and contain a positively charged amino acid on at least a majority of the positions 1, 3, 5, 7, 9 (11, 13, 15, 17, 19, 21, 23 and 25) and an uncharged amino acid on at least a majority of the positions 2, 4, 6, 8, 10, (12, 14, 16, 18, 20, 22, 24). Such a β-strand is laterally amphipathic and has a maximum hydrophobic moment at 180°. The β-strand structure is flatter than the α-helix and, stated simply, is hydrophobic on the left and hydrophilic on the right or vice versa. These are "type V" peptides.

The positively charged amino acids are preferably chosen from the group consisting of ornithine (O), lysine (K), arginine (R) and histidine (H), while the uncharged amino acids are preferably chosen from the group consisting of the aliphatic amino acids glycine (G), alanine (A), valine (V), leucine (L), isoleucine (I), the amino acids with a dipolar side chain methionine (M), asparagine (N), glutamine (Q), serine (S), threonine (T), the amino acids with an aromatic side chain phenylalahine (F), tyrosine (Y), tryptophan (W). Amino acids on the border between hydrophilic and hydrophobic can be chosen from both groups or from the remaining amino acids.

Hardly any difference in activity can in principle be detected when one of the positive amino acids and/or one of the uncharged amino acids is replaced by a random amino acid. The majority of the positively charged amino acids is therefore preferably the total number of positively charged amino acids minus 1 and the majority of the uncharged amino acids is preferably the total number of uncharged amino acids minus 1.

The domain can be a part of a larger peptide but can itself also make up the entire peptide. When the domain forms part of a larger peptide, the C-terminal and/or N-terminal amino acids which are then additionally present can be random amino acids.

The following peptides of the type I are particularly recommended:

| | | |
|---|---|---|
| KRLFKELKFSLRKY | (peptide 3) | (SEQ ID NO: 1) |
| KRLFKELLFSLRKY | (peptide 4) | (SEQ ID NO: 2) |
| KRLFKELKKSLRKY | (peptide 5) | (SEQ ID NO: 3) |
| KRLFKELLKSLRKY | (peptide 6) | (SEQ ID NO: 4) |
| OOLFOELOOSLOOY | (peptide 7) | (SEQ ID NO: 5) |
| OOLFOELLOSLOOY | (peptide 8) | (SEQ ID NO: 6) |
| KRLFKKLKFSLRKY | (peptide 9) | (SEQ ID NO: 7) |
| KRLFKKLLFSLRKY | (peptide 10) | (SEQ ID NO: 8) |

A preferred peptide of the type Ill has the following amino acid sequence:

LLLFLLKKRKKRKY (peptide 11) (SEQ ID NO: 9)

The peptides according to the invention can also contain further modifications. These modifications are for instance an N-termninal amide ring, for instance with acetic acid anhydride, or an alternative cleavage of the synthesis resin by which the C-terminus is modified. For this latter a replacement of the C-terminal carboxylic acid group by an amide, ester, ketone, aldehyde or alcohol group can be envisaged. Peptides with such a modification are for instance:

KRLFKELKFSLRKY-amide (peptide 12) (SEQ ID NO: 10)

KRLFKELLFSLRKY-amide (peptide 13) (SEQ ID NO: 11)

In addition to single peptides, oligomers can also be made. These are preferentially linear oligomers of the peptides according to the invention. The coupling can be head-to-head and tail-to-tail as well as head-to-tail, either by direct synthesis or post-synthetic enzymatic coupling. For a trans-membrane pore formation a minimum peptide length is required. Oligomers of the peptides according to the invention are double length and are thereby better able in principle to span the whole phospholipid double layer of the bacterial cell membrane at one time. The activity of the peptide could hereby improve even further. In addition, extension of the peptides provides stabilisation of the helix conformation. A spacer must usually be inserted. In direct synthesis of head-to-tail coupled oligomers a spacer can be inserted to size by the use of a chain of unnatural amino acids of the correct length, for instance β-alanine, γ-amino butyric acid, ε-amino caproic acid, etc. Heterodifuctional coupling reagents, such as are commercially available for coupling peptide antigens to carrier proteins (for instance 1-ethyl-3-[3-dimethylaminopropyl]carbodiimide (EDC), m-maleimidobenzoyl]-N-hydroxysuccinimide ester (MBS), N-succinimidyl 3-[pyridyldithio]propionate (SPDD) etc.) are used to make linear oligomers with an inserted spacer. For head-to-tail and tail-to-tail couplings can be used trivalent amino acids such as asparagine acid (D), glutamine acid (E), ornithine (O), lysine (K), serine (S), cysteine. Such oligomers are for instance:

KRKFHEKHHSHRGYC-CYGRHSHHKEHFKRK (peptide 14) (SEQ ID NO: 12)

YGRHSHHKEHFKRKC-CKRKFHEKHHSHRGY (peptide 15) (SEQ ID NO: 13)

$^\alpha$N,$^\epsilon$N-(KRKFHEKHHSHRGY)$_2$K-amide (peptide 16) (SEQ ID NO: 14)

$^\alpha$N,$^\epsilon$N-(KRLFKELKFSLRKY)$_2$K-amide (peptide 17) (SEQ ID NO: 15)

$^\alpha$N,$^\epsilon$N-(KRLFKKLKFSLRKY)$_2$K-amide (peptide 18) (SEQ ID NO: 16)

Peptides 14 and 15 are obtained by synthesis of peptide 2 with an additional C-terminal respectively N-terminal cysteine, whereafter the oligomer is obtained by air oxidation. Peptides 16, 17 and 18 are obtained by making use of the Multiple Antigenic Peptide (MAP) strategy, wherein a lysine having on both the α- and on the ε-amino group an Fmoc protection was used as first amino acid on the synthesis resin, whereby two identical amino acid chains (peptides 2, 3 and 9) were synthesized simultaneously on one lysine molecule.

The peptides described herein have no or hardly any haemolytic activity in physiological buffers such as PBS (phosphate-buffered saline solution). A low activity against erythrocytes of human origin is an indication of low toxicity. This selectivity is essential for the use of these peptides as antibiotics.

The peptides according to the invention can be used in or as an antibacterial agent, in or as an antifungal agent and in or as an agent against infection by yeasts. Their activity will be further illustrated in the accompanying examples.

The invention therefore further relates to the peptides for use as antibacterial agent, for use as antifungal agent and for use as anti-mycotic agent.

Also part of the invention is the use of the peptides for the manufacture of a medicine for the treatment of bacterial infections and for the manufacture of a medicine for the treatment of fungal infections and/or infection by yeasts.

The peptides according to the invention can be used in different pharmaceutical forms of administration. Particularly recommended are spray, ointment, gel and lozenges. These forms of administration can be used to control yeasts, such as Candida, bacteria in the oral cavity, on the skin, in cattle or in food, and fungi.

The invention is further illustrated in the accompanying examples, which are only given by way of illustration and not to limit the invention in any way whatever.

EXAMPLES

Example 1

Peptide Synthesis

Peptides according to the invention were chemically synthesized as described by Van 't Hof et al. (1991) and Helmerhorst et al. (1997). Peptides were synthesized using the T-bag method, which was adapted for 9-fluorenylmethoxycarbonyl ((Fmoc) chemistry). p-Benzyloxybenzyl alcohol resins to which the first N-Fmoc protecting amino acids were already coupled, were arranged in the T-bags. The coupling reactions were performed in N,N-dimethyl formamide. After completion of the amino acid chain it was cleaved from the resin and the side chain protection groups were simultaneously removed with a mixture of 5% thioanisole, 5% phenol, 5% water and 85% trifluoroacetic acid. Purity analyses were performed by reversed-phase HPLC and showed one single peak with only few contaminants (less than 5%).

All peptides were dissolved in 10 mM potassium phosphate buffer (PPB), pH 7.0, to a concentration of 2 mg/ml and stored at −80° C. The final pH of the stock solution was 6.0. The exact peptide concentrations which were used in the antibacterial assay were determined by amino acid analysis.

Table 1 gives an overview of the peptides 2 to 13 which were made in this manner. Peptides 1 and 2 from this table show respectively the histatin 5 and the C-terminal part thereof. Amino acids in bold type are changes relative to peptide 2.

Example 2

Antibacterial Activity Against Monocultures in vitro

Monocultures of the bacteria Streptococcus mutans (R9), Strentococcus sanguis (SB 179), Streptococcus salivarius (SS 196), Actinomyces naeslundii (WVU 627), Fusobacterium nucleatum (ATCC 10953), Prevotella intermedia (T588) and Veillonella parvula (ATCC 17745) were cultured to a late log phase in BHI (Difco), washed three times in 10 mM potassium phosphate buffer (PPB) and diluted to a suspension of $10^6$ CFU/ml. In polypropylene Eppendorf cups (Costar) 250 μl of this suspension was mixed in duplicate with 250 μl of an antimicrobial peptide solution according to the invention (The final peptide concentration was 100 μg/ml) and incubated for half an hour at 37° C. under aerobic conditions. The control treatment was performed in 10 mM without peptide.

After incubation the samples were centrifuged, 400 μl of the supernatant was removed and 400 μl PBS (9 mM sodium phosphate pH 7.0 in 150 mM NaCl), in which the peptides are inactive, was added. The samples were further diluted in PBS and 50 μl of tenfold and thousand-fold dilutions were plated out on blood agar (Difco) to perform viability counts.

The result of the tests is shown in table 2. This shows that the peptides according to the invention have a clearly higher activity have than the naturally occurring histatin 5.

TABLE 1

| Peptide | Sequence | |
|---|---|---|
| 1 | DSHAKRHHGYKRKFHEKHHSHRGY | (SEQ ID NO: 17) |
| 2 | KRKFHEKHHSHRGY | (SEQ ID NO: 18) |
| 3 | KRLFKELKFSLRKY | (SEQ ID NO: 1) |
| 4 | KRLFKELLFSLRKY | (SEQ ID NO: 2) |
| 5 | KRLFKELKKSLRKY | (SEQ ID NO: 3) |
| 6 | KRLFKELLKSLRKY | (SEQ ID NO: 4) |
| 7 | OOLFOELOOSLOOY | (SEQ ID NO: 5) |
| 8 | OOLFOELLOSLOOY | (SEQ ID NO: 6) |
| 9 | KRLFKKLKFSLRKY | (SEQ ID NO: 7) |
| 10 | KRLFKKLLFSLRKY | (SEQ ID NO: 8) |
| 11 | LLLFLLKKRKKRKY | (SEQ ID NO: 9) |
| 12 | KRLFKELKFSLRKY-amide | (SEQ ID NO: 10) |
| 13 | KRLFKELLFSLRKY-amide | (SEQ ID NO: 11) |
| 14 | KRKFHEKHHSHRGYC-CYGRHSHHKEHFKRK | (SEQ ID NO: 12) |
| 15 | YGRHSKKKEHFKRKC-CKRKFHEKHHSHRGY | (SEQ ID NO: 13) |
| 16 | $^{\alpha}$N, $^{\epsilon}$N-(KRKFHEKHHSHRGY)$_2$K-amide | (SEQ ID NO: 14) |
| 17 | $^{\alpha}$N, $^{\epsilon}$N-(KRLFKELKFSLRKY)$_2$K-amide | (SEQ ID NO: 15) |
| 18 | $^{\alpha}$N, $^{\epsilon}$N-(KRLFKKLKFSLRKY)$_2$K-amide | (SEQ ID NO: 16) |

TABLE 2

% reduction in viability counts

| bacteria | buffer[1] | histatin 5 | peptide 3 | peptide 10 | positive control peptide |
|---|---|---|---|---|---|
| S. mutans | 0.00 (22.6) | −49.5 (68.5) | >99.9* | >99.9* | >99.9 |
| S. sanguis | 0.00 (49.4) | 69.5 (4.5) | 99.6 (0.30)* | >99.9* | >99.9* |
| S. salivarius | 0.00 (36.3) | 38.3 (44.1) | >99.9* | >99.9* | >99.9* |
| A. naeslundii | 0.00 (23.7) | −11.6 (3.9) | >99.9* | >99.9* | >99.9* |
| V. parvula | 0.00 (16.7) | 26.9 (49.3) | >99.9* | >99.9* | >99.9* |
| F. nucleatum | 0.00 (15.9) | 49.3 (4.5)* | 92.9 (3.00)* | 99.2 (0.84)* | >99.9* |
| P. intermedia | 0.00 (4.69) | −235 (196) | −57.8 (77.9) | 81.0 (21.4)* | 98.0 (1.0)* |

[1]The treatment with buffer was normalized at 0.00% killing. The standard deviation from the average is shown in brackets,
*significantly higher killing than the samples which were only administered buffer Example 3
Growth Inhibition The growth of the yeast Candida albicans, Torulopsis glabrata and meticillin-resistant Staphylococcus aureus (MRSA) was tested by growing them on agar on which 10 μg of each of the peptides according to the invention was spotted. Table 3 shows the result. "+" designates full growth inhibition, "+/−" designates partial inhibition and "−" signifies no inhibition.

TABLE 3

| peptide | C. albicans | T. glabrata | MRSA |
|---|---|---|---|
| histatin 5 | − | − | − |
| dh-5 | − | − | − |
| peptide 3 | + | + | +/− |
| peptide 4 | + | + | +/− |
| peptide 5 | + | + | n.d. |
| peptide 6 | + | + | n.d. |
| peptide 7 | + | + | n.d. |
| peptide 8 | + | + | n.d. |

TABLE 3-continued

| peptide | C. albicans | T. glabrata | MRSA |
|---|---|---|---|
| peptide 9 | + | + | + |
| peptide 10 | + | + | + |
| peptide 11 | + | + | + |
| peptide 12 | + | + | n.d. |
| peptide 13 | + | + | n.d. |

*not done

Example 4
Inhibition of Lactic Acid Production

All peptides according to the invention were tested for their capacity to inhibit the lactic acid production of the bacteria Streptococcus sanguis, Streptococcus mutans, Streptococcus salivarius and Lactobacillus rhamnosus. The formation of lactic acid is a measure for the metabolic activity.

For this purpose cultures of bacteria cells were incubated for 1 hour in 10 mM PPB with 0.5 glucose and different concentrations of the peptides. The formation of lactic acid was monitored by means of spectrophotometry. Table 4 shows the result. "+" designates full inhibition at 4–20 μg/ml peptide, "−" signifies no inhibition of lactic acid formation at >100 μg/ml peptide.

TABLE 4

| peptide | S. sanguis | S. mutans | S. salivarius | L. rhamnosus |
|---|---|---|---|---|
| histatin 5 | − | − | − | − |
| dh-5 | − | − | − | − |
| peptide 3 | + | + | + | + |
| peptide 4 | + | + | + | + |
| peptide 5 | + | + | + | + |
| peptide 6 | + | + | + | + |
| peptide 7 | + | + | + | + |
| peptide 8 | + | + | + | + |
| peptide 9 | + | + | + | + |
| peptide 10 | + | + | + | + |
| peptide 11 | + | + | + | + |
| peptide 12 | + | + | + | + |
| peptide 13 | + | + | + | + |

Example 5
Killing of Yeasts $5*10^6$ cells of Candida pseudotropicalis, Candida albicans 10231, Cryptococcus neoformans, Candida krusei, Candida parapsilosis, Candida glabrata and Candida albicans 32354 and an ergosterol-deficient mutant thereof were incubated for one and a half hours at 37° C. in the presence of a dilution series of a peptide according to the invention or amphotericin B in 1 mM potassium phosphate buffer, pH 7.0. The viability was determined by plating out. Used as positive control was synthetic PGLa ("Protein beginning with Glycine and ending with Leucin-amide", with the amino acid sequence GHMASKGAIAGKIAKVALKAL-amide). (SEQ ID NO: 17) The negative control was a peptide consisting of the residues 1 to 14 of synthetic cystatin S (SSSKEENRIIPGGI. (SEQ ID NO: 18) Amphotericin is a known anti-mycotic medication. There is however one Candida albicans mutant (of strain 32354), which has no ergosterol in its cell membrane and which is resistant to amphotericin B. $IC_{50}$ values are peptide concentrations wherein 50% of the inoculum is killed. Table 5 shows the result.

TABLE 5

| | peptide 10 | positive control | negative control | amphotericin B |
|---|---|---|---|---|
| IC$_{50}$ values (μg/ml) | | | | |
| C. pseudotropicalis | 2 | 1 | >67 | 8 |
| C. albicans 10231 | 1 | 1 | >67 | 1 |
| Cr. neoformans | 1 | 0.5 | >67 | 1 |
| C. krusei | 0.3 | 1 | >67 | >70 |
| C. parapsilosis | 2 | 1 | >67 | 6 |
| C. glabrata | 2 | 9 | >67 | 2 |
| C. albicans 32354 | 0.5 | 1 | n.d. | 2 |
| C. albicans 32354, ergosterol-deficient mutant | 1 | 3 | n.d | >70 |

Example 6

Antibacterial Activity in an Artificial Oral Biofilm

An artificial oral biofilm was made by placing hydroxyapatite discs for five days in a continuous culture system of seven oral aerobic and anaerobic types of bacteria (*Streptococcus mutans, Streptococcus sanpuis, Streptococcus salivarius, Actinomyces naeslundii, Veillonella parvula, Prevotella intermedia* and *Fusobacterium nucleatum*)

The discs with the biofilm formed thereon were subsequently incubated for half an hour with different concentrations of peptide in 10 mM potassium phosphate buffer, pH 7.0. The biofilm was then sonicated from the discs, diluted in PBS and plated out on semi-selective agar plates. The total anaerobic counts were counted (Streptococci+ Actinomyces) on aerobic incubated blood agar plates, the total Gram-negative counts (Veilonella, Fusobacterium and Prevotella) on vancomycin-containing plates and the total counts on the anaerobic incubated blood agar. An inactive peptide of the Von Ebner's Gland Protein (VEGh, 3-21: LLASDEEIQDVSGTWYLKA) (SEQ ID NO: 19) was used as negative control.

The results are shown in table 6. Herein "*" signifies that killing is significantly higher than of the negative control (p<0.05)

TABLE 6

| treatment | concentration | total aerobic average (s.d.) | total anaerobic average (s.d.) | total Gram-negative average (s.d.) |
|---|---|---|---|---|
| % reduction in viability counts | | | | |
| buffer | | 0.00 (70.7) | 0.00 (57.2) | 0.00 (50.4) |
| peptide 9 | 10 μg/ml | −67.4 (134.4) | −66.2 (143.6) | 51.0 (32.0)* |
| | 100 μg/ml | 78.7 (25.6)* | 51.2 (53.9)* | 30.6 (104.4)* |
| | 250 μg/ml | 64.8 (48.4)* | 61.2 (49.2)* | 53.3 (70.7) |
| | 500 μg/ml | 96.6 (4.0)* | 93.2 (4.1)* | 96.9 (0.85)* |
| peptide 10 | 10 μg/ml | 29.9 (53.4) | 54.3 (15.6)* | 59.3 (41.0)* |
| | 100 μg/ml | 71.4 (26.7)* | 42.5 (52.3)* | 47.8 (50.0)* |
| negative control peptide | 100 μg/ml | 96.6 (62.4) | −71.7 (40.0) | 41.5 (183.6) |

TABLE 6-continued

| treatment | concentration | total aerobic average (s.d.) | total anaerobic average (s.d.) | total Gram-negative average (s.d.) |
|---|---|---|---|---|
| % reduction in viability counts | | | | |
| Chlorhexidine | 35 ppm | 39.0 (71.8) | 38.4 (632) | 68.3 (196)* |
| | 200 ppm | 99.9 (0.00)* | 99.9 (0.00)* | 99.9 (0.00)* |

Example 7

Antimicrobial Activity on Oral Bacteria

In order to determine whether the peptides according to the invention are also active against bacteria such as are encountered in the mouth, bacteria were collected from saliva and plaque. Saliva was shaken on a vortex mixer and centrifuged. The pellet was washed with 10 mM potassium phosphate buffer and incubated for half an hour at 37° C. with buffer (negative control), peptide 10 (100 μg/ml; invention), PGLa (100 μg/ml; positive control) and chlorhexidine (50 ppm). Table 7 shows the result.

TABLE 7

| bacteria | treatment | total aerobic average (s.d.) | total anaerobic average (s.d.) | total Gram-negative average (s.d.) |
|---|---|---|---|---|
| % reduction in viability counts | | | | |
| saliva | buffer | 0.00 (27.7) | 0.00 (37.1) | 0.00 (23.3) |
| | peptide 10 | 51.2 (31.5)* | 71.8 (20.8)* | 92.5 (9.15)* |
| | positive control peptide | 60.1 (30.0)* | 73.2 (12.6)* | 97.7 (1.52)* |
| | Chlorhexidine | >99.9* | >99.9* | >99.9* |
| plaque | buffer | 0.00 (63.4) | 0.00 (45.7) | 0.00 (90.4) |
| | peptide 10 | 66.7 (7.17) | 53.6 (30.6) | 96.1 (3.02)* |
| | positive control peptide | 58.5 (18.7) | 51.5 (44.9) | 84.0 (11.0)* |
| | Chlorhexidine | 99.7 (0.3)* | 99.7 (0.2)* | 99.7 (0.3)* |
| disrupted plaque | buffer | 0.00 (46.0) | 0.00 (52.4) | 0.00 (42.7) |
| | peptide 10 | 66.9 (17.3) | 57.5 (38.9)* | 80.8 (24.7)* |
| | positive control peptide | 41.7 (54.4) | 68.5 (31.9)* | 45.9 (77.2)* |
| | Chlorhexidine | 99.7 (0.3)* | 99.0 (1.42)* | >99.9* |
| cultured plaque | buffer | 0.00 (25.7) | 0.00 (61.5) | 0.00 (45.7) |
| | peptide 10 | 30.7 (50.7) | 84.5 (8.75)* | 28.3 (46.7) |
| | positive control peptide | 20.6 (77.4) | 87.2 (9.87)* | 83.7 (7.30)* |
| | Chlorhexidine | >99.9* | >99.9* | >99.9* |

Example 8

Killing of Bacteria by Peptide 10 Compared with Histatin 5

$10^6$ bacteria of the types Klebsiella (ATCC 43816) and *Pseudomonas aeruainosa* (PA01, clinical isolate) were incubated for 1 hour at 37° C. in 10 mM sodium phosphate buffer with 1% tryptic soy broth (pH 7.4) in the presence of 25 or 50 μg/ml histatin 5, 3.12, 6.25, 12.5, 25 or 50 μg/ml peptide 10, 10 μg/ml protegrin (positive control), 50 μg/ml peptide 4 or no peptide (both negative controls). Further included was a blank which was not incubated for an hour at 37° C. (t=0 min). The colony forming units of each sample were then determined by means of plating on DST (Diagnostic Sensitivity Test).

FIG. 1A shows a histogram of the number of colony forming units (CFU) of each sample with Klebsiella. FIG. 1B shows the results for Pseudomonas.

Example 9

Killing of *Candida albicans* by Peptide 10 Compared with Histatin 5 with Different Incubation Times $10^6$ Candida albicans were incubated for 1 or 3 hours at 37° C. in 10 mM sodium phosphate buffer with 1% Sabouraud (pH 7.4) in the presence of 25, 50 or 100 µg/ml histatin 5, 3.12, 6.25, 12.5, 25, 50 or 100 µg/ml peptide 10, 10 µg/ml protegrin (positive control), 50 µg/ml peptide 4 or no peptide (both negative controls). Further included was a blank which was not incubated for one hour at 37° C. (t=0 min). The colony forming units of each sample were then determined as described above with Sabouraud plates.

Figure 2B:
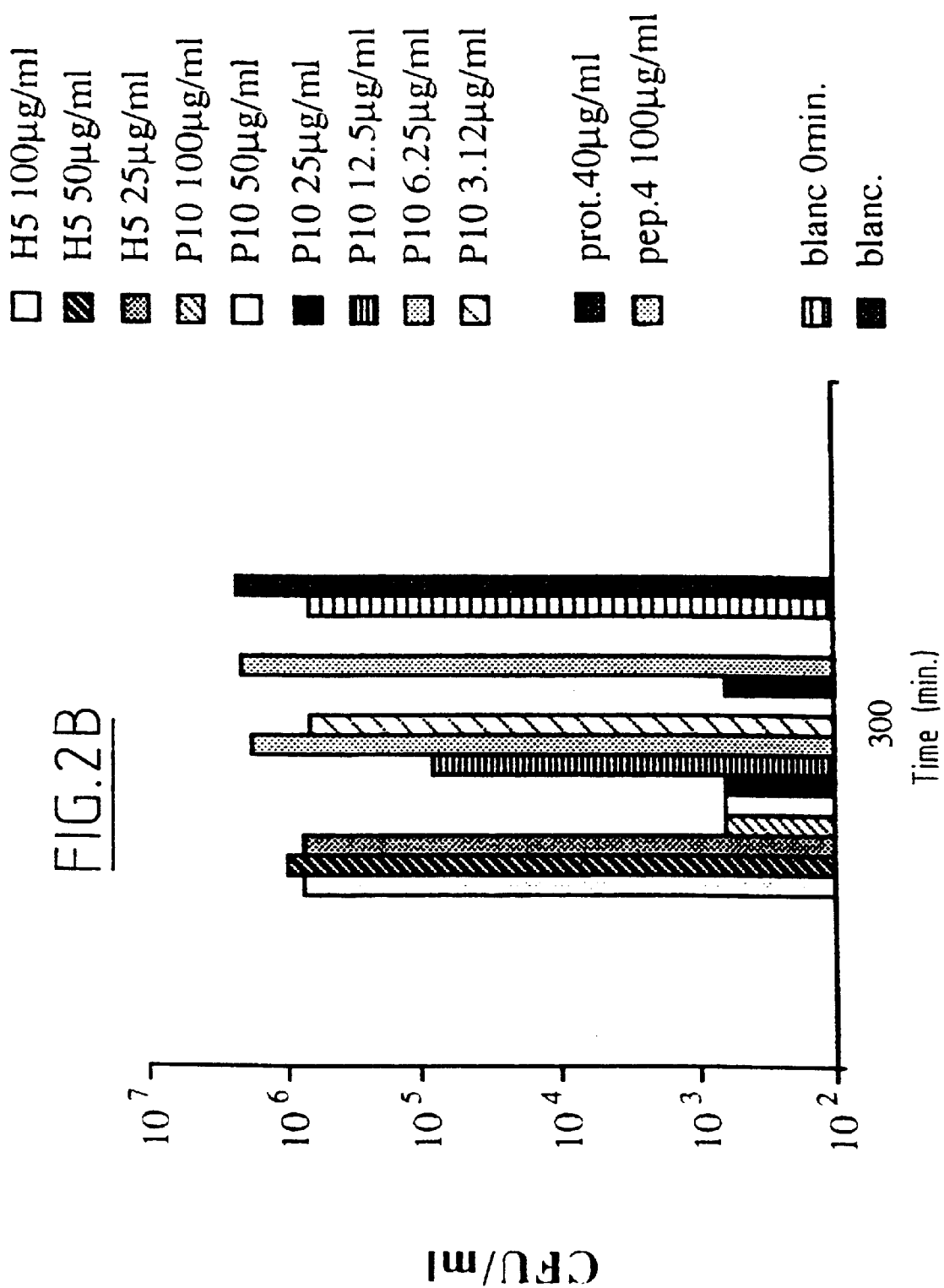

FIG. 2A shows a histogram of the number of colony forming units (CFU) of each sample after 1 hour of incubation. FIG. 2B gives the results for 3 hours of incubation.

Example 10

Killing of Salmonella and Yersinia Species by Peptide 10

Figure 3A:
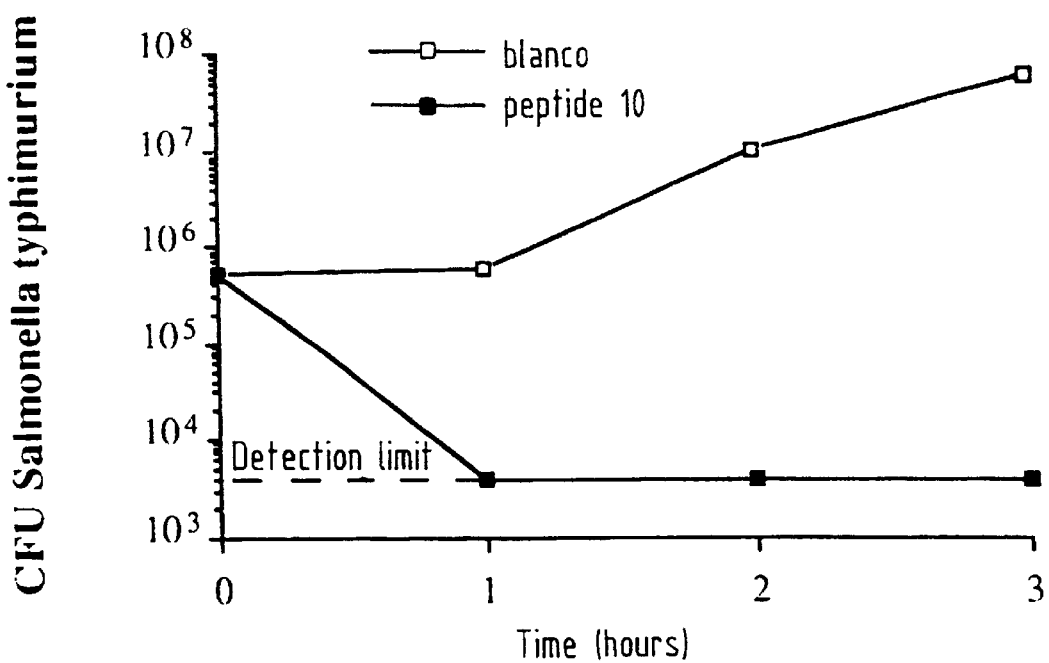
Figure 3B:
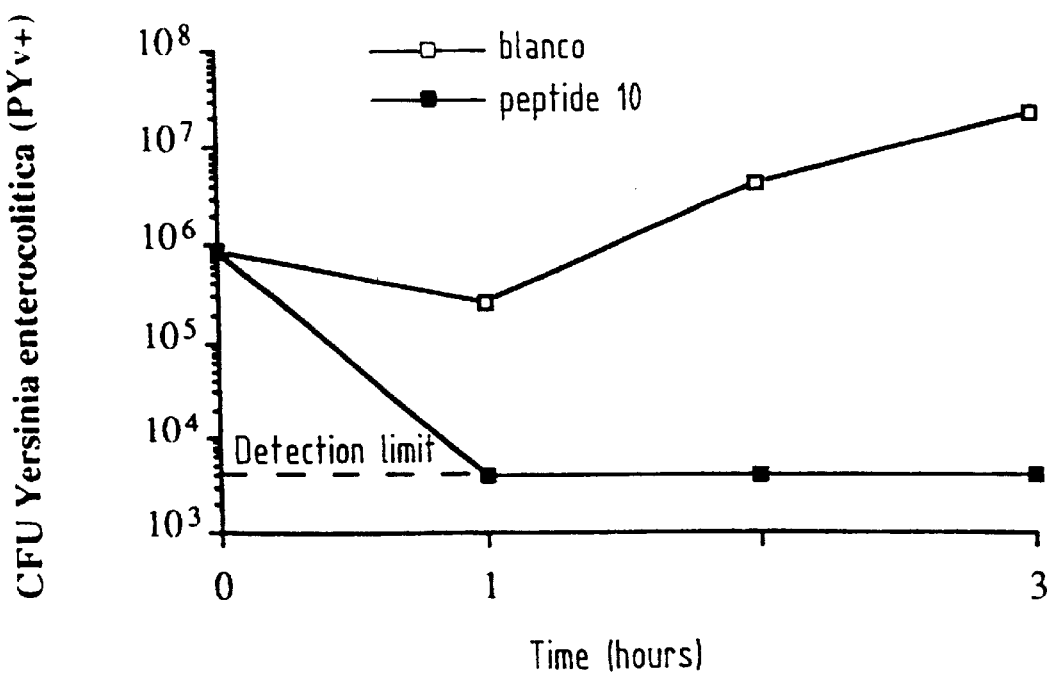

Peptide 10 was added in a concentration of 50 µg/ml to a culture with $10^4$ *Salmonella typhimurium* bacteria. For control purposes a culture to which nothing was added was included as blank. The number of CFU was determined at the points in time 0, 1, 2 and 3 hours. The same was done with *Yersinia enterocolitica* (PYv+). From FIGS. 3A respectively 3B can be seen that by adding peptide 10 the number of bacteria fell to below the detection limit. As can be seen from the above examples, the peptides according to the invention have a considerably higher antibacterial, antimycotic and antifungal activity than the naturally occurring histatin 5. Particular peptides are also found to have a killing effect on micro-organisms which are resistant to antimicrobial agents used at present.

What is claimed is:

1. Peptides with antimicrobial activity consisting of an amino acid chain which contains a domain of 10 to 25 amino acids, wherein the majority of the amino acids of one half of the domain are positively charged amino acids and the majority of the amino acids of the other half of the domain are uncharged amino acids, characterized in that the peptides comprise an amino acid sequence:

LLLFLLKKRKKRKY (peptide 11) (SEQ ID NO:9).

2. Peptides as claimed in claim 1, wherein the N-terminus is amidated.

3. Peptides as claimed in claim 1, wherein the C-terminus is an amide, ester, ketone, aldehyde or alcohol group.

4. Oligomers of two or more peptides as claimed in claim 1.

5. Peptides as claimed in claim 1, for use as an antibacterial agent.

6. Peptides as claimed in claim 1, for use as an antifungal agent.

7. Peptides as claimed in claim 1, for use as an antimycotic agent.

8. Pharmaceutical composition comprising the peptides as claimed in claim 1, and one or more suitable excipients.

9. Pharmaceutical composition as claimed in claim 8, in the form of a spray, ointment, gel or lozenge.

* * * * *